(12) United States Patent
Mukai et al.

(10) Patent No.: US 9,668,925 B2
(45) Date of Patent: Jun. 6, 2017

(54) ABSORBENT ARTICLE

(71) Applicant: UNICHARM CORPORATION, Ehime (JP)

(72) Inventors: Hirotomo Mukai, Kagawa (JP); Takeshi Shimazu, Kagawa (JP)

(73) Assignee: Unicharm Corporation, Ehime (JP)

(*) Notice: Subject to any disclaimer, the term of this patent is extended or adjusted under 35 U.S.C. 154(b) by 124 days.

(21) Appl. No.: 14/432,460

(22) PCT Filed: Sep. 30, 2013

(86) PCT No.: PCT/JP2013/076587
§ 371 (c)(1),
(2) Date: Mar. 30, 2015

(87) PCT Pub. No.: WO2014/054594
PCT Pub. Date: Apr. 10, 2014

(65) Prior Publication Data
US 2015/0238368 A1 Aug. 27, 2015

(30) Foreign Application Priority Data
Oct. 1, 2012 (JP) .................................. 2012-219391

(51) Int. Cl.
*A61F 13/49* (2006.01)
*A61F 13/496* (2006.01)
*A61F 13/84* (2006.01)

(52) U.S. Cl.
CPC ...... *A61F 13/49061* (2013.01); *A61F 13/496* (2013.01); *A61F 13/49009* (2013.01); *A61F 13/84* (2013.01); *A61F 2013/49098* (2013.01)

(58) Field of Classification Search
CPC .......... A61F 13/49009; A61F 13/49011; A61F 13/4906; A61F 13/49061; A61F 13/493; (Continued)

(56) References Cited

U.S. PATENT DOCUMENTS 5,383,867 A * 1/1995 Klinger ................ A61F 5/4401
604/358
5,569,229 A * 10/1996 Rogers .................... A61F 13/42
604/358
(Continued)

FOREIGN PATENT DOCUMENTS

EP  1 723 939 A1  11/2006
JP  10-337300     12/1998
(Continued)

OTHER PUBLICATIONS

International Search Report from corresponding PCT application No. PCT/JP2013/076587 dated Dec. 3, 2013 (3 pgs).
(Continued)

*Primary Examiner* — Lynne Anderson
(74) *Attorney, Agent, or Firm* — Brinks Gilson & Lione

(57) ABSTRACT

A disposable diaper having: an absorbent main body having an absorber; and an exterior body including an exterior body sheet which is disposed in an outward direction than the absorbent main body. On a face of an outer direction's side of the disposable diaper, an opening unit into which a finger can be inserted is formed. The exterior body has an overlap region which overlaps with an absorber, and the opening unit is provided in the overlap region.

10 Claims, 9 Drawing Sheets

(58) Field of Classification Search
CPC .... A61F 13/496; A61F 13/505; A61F 13/655; A61F 2013/49063; A61F 2013/49098; A61F 2013/5055
USPC .................................................. 604/385.09
See application file for complete search history.

(56) References Cited

U.S. PATENT DOCUMENTS

| | | | | |
|---|---|---|---|---|
| 5,843,065 | A * | 12/1998 | Wyant | A61F 13/505 604/385.09 |
| 7,175,613 | B2 * | 2/2007 | Sugiyama | A61F 13/493 604/385.01 |
| 7,494,483 | B2 * | 2/2009 | Beck | A61F 13/15203 604/385.01 |
| 7,887,523 | B2 * | 2/2011 | Sasayama | A61F 13/49011 604/385.01 |
| 8,092,442 | B2 * | 1/2012 | Sukegawa | A61F 13/4915 604/385.14 |
| 8,696,642 | B1 * | 4/2014 | Price | A61F 13/4915 604/385.09 |

FOREIGN PATENT DOCUMENTS

| | | |
|---|---|---|
| JP | 11-335903 | 12/1999 |
| JP | 2007-330543 | 12/2007 |
| WO | WO 02/069865 A1 | 9/2002 |
| WO | WO 2009/119740 A1 | 10/2009 |
| WO | WO 2011/108286 A1 | 9/2011 |
| WO | WO 2011/145626 A1 | 11/2011 |
| WO | WO 2012/029294 A1 | 3/2012 |

OTHER PUBLICATIONS

European extended Search Report from corresponding European application No. 13844431.0 dated May 30, 2016 (6 pgs).
Japanese Notification of Reasons for Refusal and English translation from corresponding Japanese application No. 2012-219391 dated Jul. 12, 2016 (4 pgs).

* cited by examiner

ABSORBENT ARTICLE

RELATED APPLICATION

This application is a 35 U.S.C. §371 national phase filing of International Patent Application No. PCT/JP2013/076587, filed Sep. 30, 2013, through which and to which priority is claimed under 35 U.S.C. §119 to Japanese Patent Application No. 2012-219391, filed Oct. 1, 2012, the entire disclosure of which is hereby expressly incorporated by reference.

TECHNICAL FIELD

The present invention relates to an absorbent article such as a disposable diaper.

BACKGROUND ART

In Patent Literature 1, in an absorbent article as a disposable diaper of a pants-type, there is known an absorbent article at which pockets for hooking hands or the like are formed (refer to Patent Literature 1, for example). According to such an absorbent article as mentioned above, a wearer and an attendant can hook his or her hands by the pocket, and easily pulls up the absorbent article.

CITATION LIST

Patent Literature

Patent Literature 1: Japanese Patent No. 4033359

SUMMARY OF INVENTION

However, the absorbent article as mentioned above has entailed the following problem. The pockets of the absorbent article described in Patent Literature 1 are disposed in the vicinity of waistline opening units of the absorbent article, and is positioned at an upper side of the absorbent article while the article is worn. Therefore, if a wearer or the like attempts to pull up the absorbent article via the pockets, the wearer or the like must lift his or her arms more upward than his or her waistline, and it has been occasionally difficult for a physically handicapped wearer to pull up the absorbent article.

Also, bodily wastes such as the wearer's urine are excreted, whereby the absorber that is disposed in a crotch region becomes heavy in weight, and the entire absorbent article may be pulled down. In such a case, the absorbent article can be pulled up via the pockets. However, the pockets are disposed in the vicinity of the waistline opening units, and are spaced from an excretion opening contact region of the absorber. Therefore, a force in an attempt to pull up the absorbent article via the pockets hardly acts on the absorber that has become heavy in weight by absorbing bodily fluid, and there has been a case in which the entire absorbent article cannot be easily pulled up.

Accordingly, the present invention has been made in view of the problem described above, and it is an object of the present invention to provide an absorbent article which can be easily pulled up by a wearer or the like.

An absorbent article according to present invention having: a longitudinal direction (longitudinal direction L) extending to a body foreside and a body backside of a wearer; a widthwise direction (widthwise direction W) which is orthogonal to the longitudinal direction; an inward direction (inward direction IN) facing a wearer; and an outward direction (outward direction OUT) opposite to the inward direction, the absorbent article comprising: a front waistline region (front waistline region S1); a back waistline region (back waistline region S2); and a crotch region (crotch region S3) which is positioned between the front waistline region and the back waistline region, the absorbent article having: an absorbent main body (absorbent main body 1A) having an absorber which is disposed at least in the crotch region; and an exterior body (exterior body 1B) including an exterior body sheet which is disposed in the outward direction than the absorbent main body, wherein an opening unit (opening unit 90) into which a finger can be inserted is formed in a face at the outward direction's side of the absorbent article, and the opening unit is provided in the overlap region (overlap region R3) which overlaps with the absorber.

DESCRIPTION OF EMBODIMENTS

Figure 1:
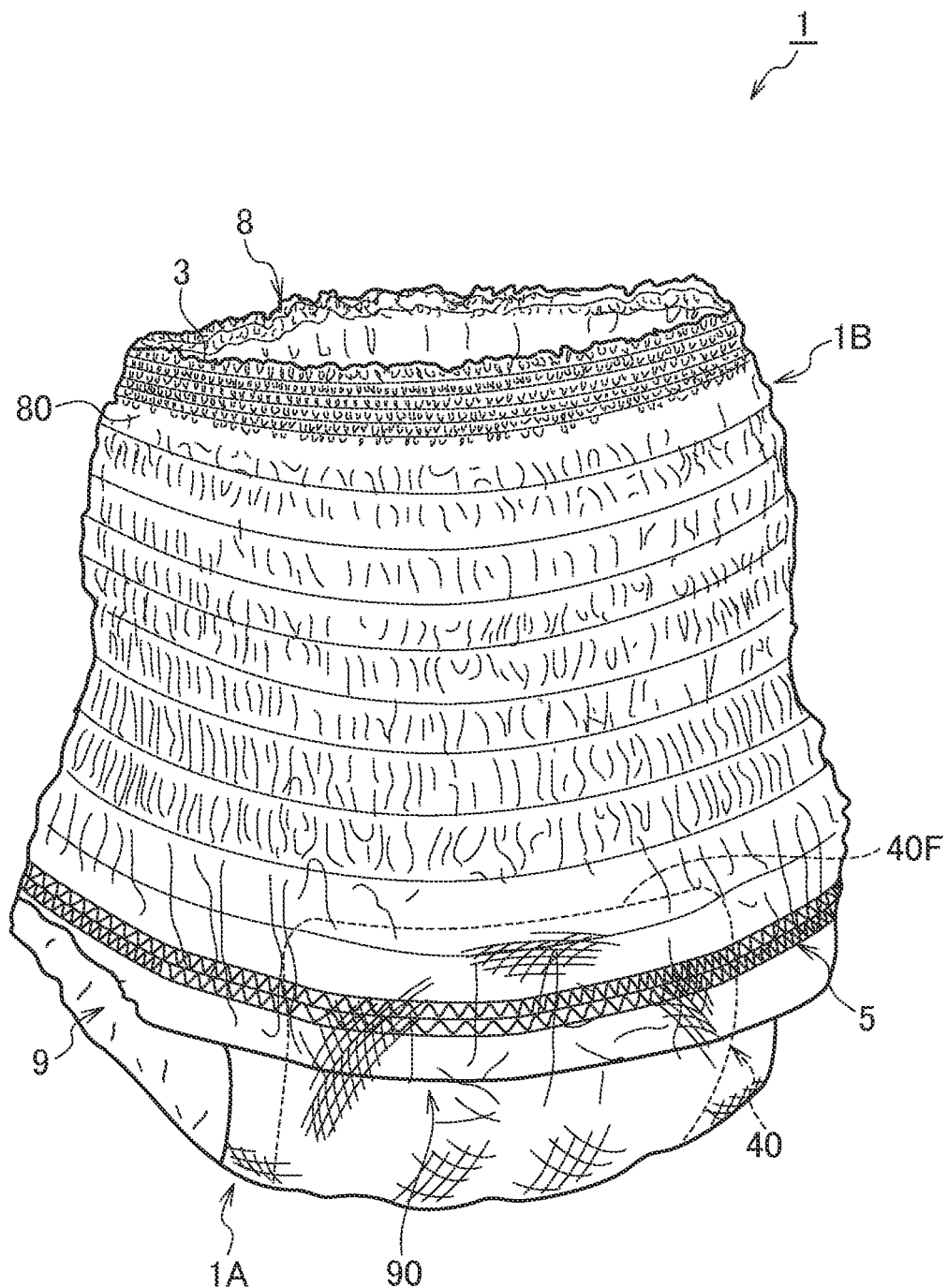
FIG. 1 is a schematic perspective view of a disposable diaper according to an embodiment.

Next, embodiments of a disposable diaper according to the embodiment will be described with reference to the drawings. It is to be noted that in the following description of the drawings, same or similar constituent elements are designated by same or similar reference numerals. However, it should be kept in mind that the drawings are schematic representations and are not drawn to scale unless otherwise specified. Moreover, the drawings do not necessarily reflect the actual dimensional relationships and ratios of component. Therefore, specific dimensions or the like should be determined in consideration of the following description. In addition, relations or ratios among such dimensions may be different from one drawing to another.

The disposable diaper according to the embodiment is characterized in that an opening unit into which fingers can be inserted is formed on a face at an outer direction's side of the absorbent article, and the opening unit is provided in an overlap region which overlaps with the absorber.

(1) Overall Schematic Structure of the Disposable Diaper

Figure 2:
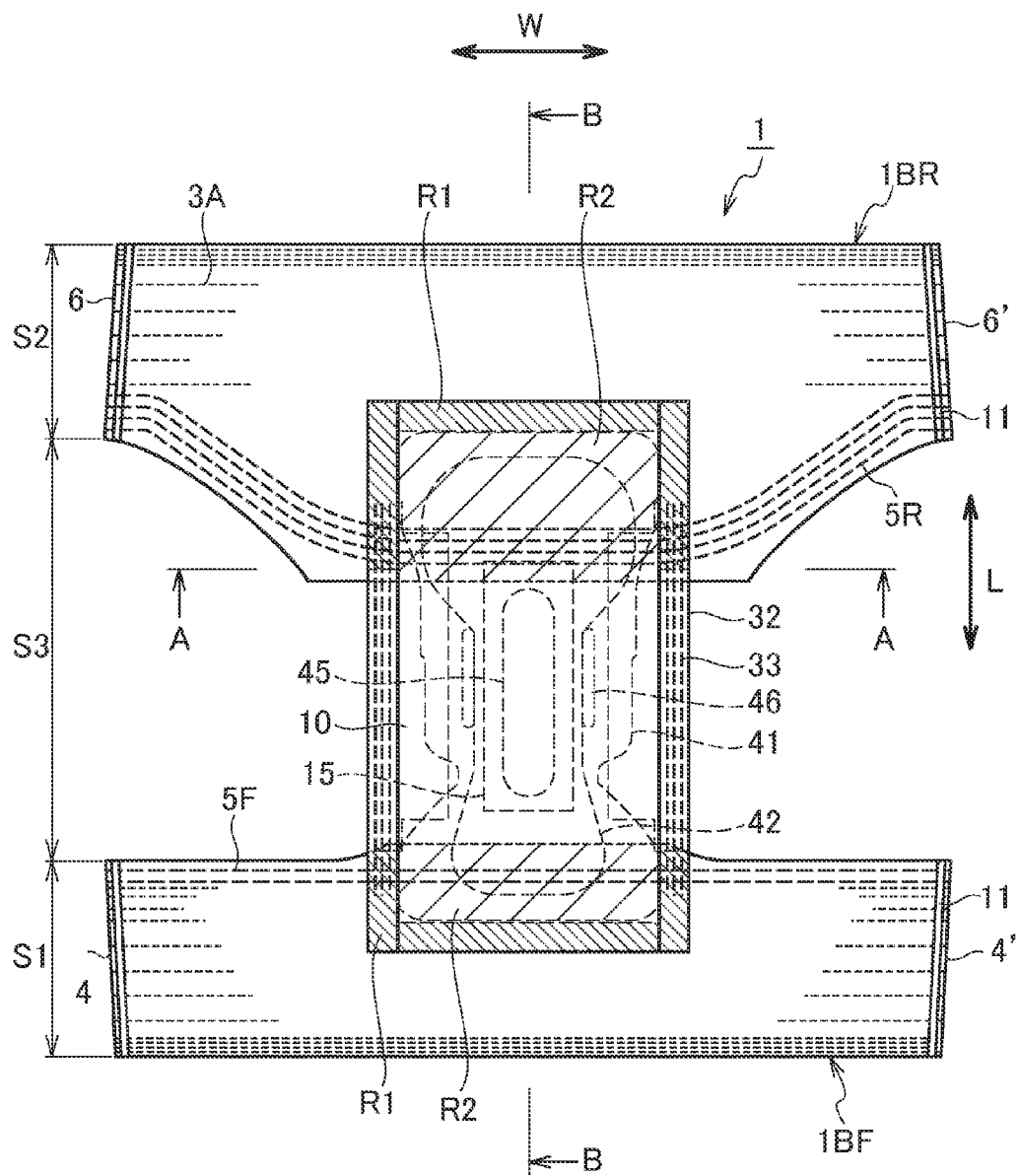
FIG. 2 is an exploded plan view of the disposable diaper according to the embodiment.
Figure 3:
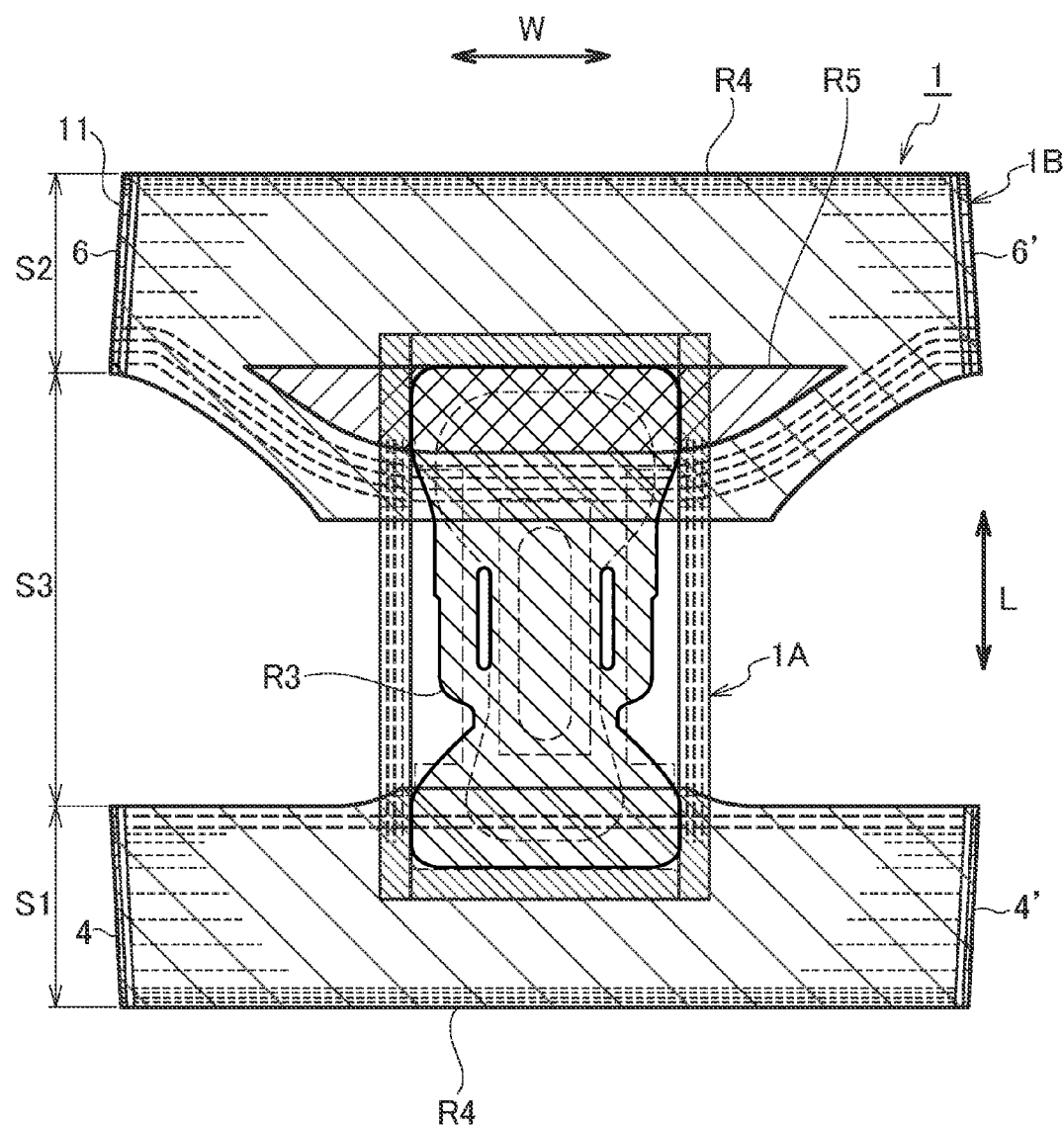
FIG. 3 is an exploded plan view of the disposable diaper according to the embodiment.
Figure 4:
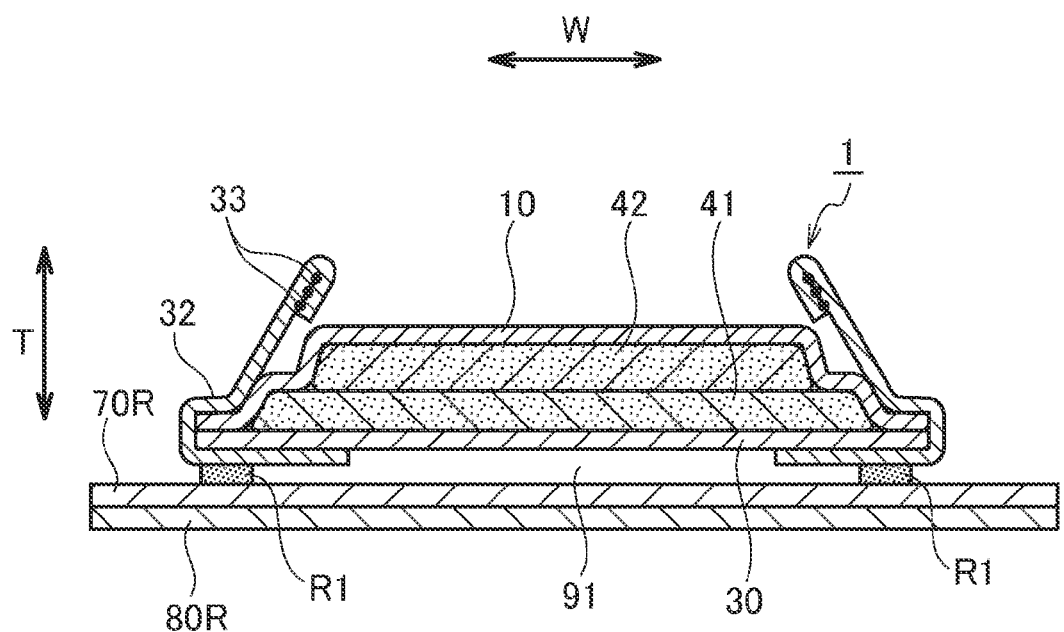
FIG. 4 is a sectional view in a widthwise direction of the disposable diaper, taken along the line A-A shown in FIG. 2.
Figure 5:
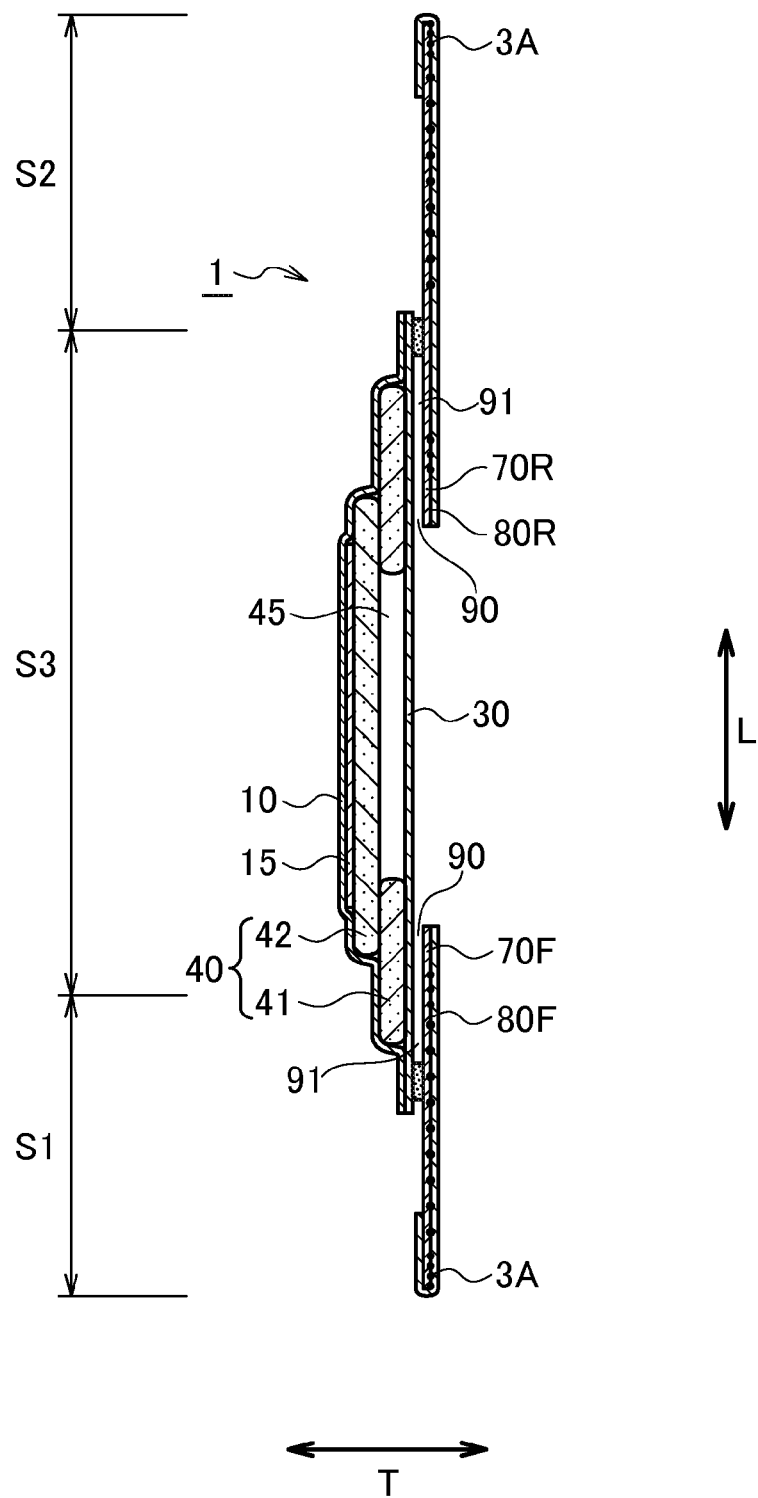
FIG. 5 is a sectional view in a longitudinal direction of the disposable diaper, taken along the line B-B shown in FIG. 2.

FIG. 1 is a perspective schematic view of a disposable diaper 1 of the embodiment. FIG. 2 and FIG. 3 each are an exploded plan views of the disposable diaper 1 according to the embodiment. FIG. 4 is a cross-sectional view in the widthwise direction of the disposable diaper 1 along the A-A line shown in FIG. 2. FIG. 5 is a cross-sectional view in the longitudinal direction of the disposable diaper 1 along the B-B line shown in FIG. 2. The disposable diaper 1 is the disposable diaper of the pants-type.

A disposable diaper 1 has: a longitudinal direction L extending to a body foreside and a body backside of a wearer; a widthwise direction W orthogonal to the longitudinal direction L; and a thickness direction T having an inward direction IN oriented to the wearer and an outward direction OUT oriented to an opposite side to the inward direction.

The disposable diaper 1, as shown in FIG. 2, has, in a longitudinal direction of the disposable diaper 1, a front waistline region S1 which corresponds to a front waistline of a wearer, a back waistline region S2 which corresponds to the back waistline of the wearer, and a crotch region S3 which corresponds to a crotch of the wearer, and is positioned between the front waistline region S1 and the rear waistline region S2.

The disposable diaper 1 includes: an absorbent main body 1A including a topsheet 10, an absorber 40, and an absorber backsheet 30 or the like; and an exterior body 1B including a foreside exterior topsheet 70F, a backside exterior topsheet 70R, and a foreside exterior backsheet 80F and a backside exterior backsheet 80R or the like, and these constituent elements are joined to each other by an adhesive or thermal fusion bonding or the like.

A front waistline edge 4 which is positioned on one outside of a widthwise direction of the exterior body 1B of the front waistline region S1 is joined with a rear waistline edge 6 which is positioned on such one outside of the widthwise direction of the exterior body 1B of the rear waistline region S2, and a front waistline edge 4' which is positioned on another outside of the widthwise direction of the exterior body 1B is joined with a rear waistline edge 6' which is positioned on such another outside of the widthwise direction of the exterior body 1B, whereby the disposable diaper 1 is formed in the shape of pants. In the front waistline region and the back waistline region of the disposable diaper of the pants-type, a joining unit 11, both edges of which are joined with each other, is formed, and a crotch region S3 is a region which is on the inside of a longitudinal direction than the joining unit 11.

In the disposable diaper 1, as shown in FIG. 1, there are formed: a waistline opening unit 8 disposed so as to surround the wearer's waistline and a pair of leg hole opening unit 9 disposed so as to surround the wearer's leg in a state in which it is formed in the shape of pants.

The exterior body 1B includes an exterior body sheet which is disposed to be outward direction's side than the absorbent main body 1A. The exterior body 1B includes: a foreside exterior topsheet 70F; a backside exterior topsheet 70R; a foreside exterior backsheet 80F; and a backside exterior backsheet 80R, and constitutes an exterior portion of the disposable diaper 1. Although the exterior body sheets of the embodiment are the foreside exterior topsheet 70F, the backside exterior topsheet 70R, the foreside exterior backsheet 80F, and the backside exterior backsheet 80R, it is sufficient if the exterior body sheet has at least one sheet member.

The exterior body 1B has: a foreside exterior body 1BF which is joined with the absorbent main body 1A and which is disposed at least in the front waistline region; and a backside exterior body 1BR which is joined with the absorbent main body 1A and which is disposed at least in the back waistline region.

The foreside exterior body 1BF is provided with the foreside exterior topsheet 70F and the foreside exterior backsheet 80F. The backside exterior body 1BR is provided with the backside exterior topsheet 70R and the backside exterior backsheet 80R. The foreside exterior topsheet 70F and the foreside exterior backsheet 80F and the backside exterior top sheet 70R and the backside exterior backsheet 80R are spaced from each other in the longitudinal direction. In the longitudinal direction, in the region in which the foreside exterior body 1BF and the backside exterior body 1BR are spaced from each other, a face of a non-skin contact side of the absorbent main body 1A is exposed.

It is to be noted that, in the exterior body, the foreside exterior body 1BF and the backside exterior body 1BR may be separated from each other, or alternatively, the foreside exterior body 1BF and the backside exterior body 1BR may be integrated with each other.

The foreside exterior topsheet 70F and the backside exterior topsheet 70R can be formed of an air-through nonwoven cloth, a spun bond nonwoven cloth, an SMS nonwoven cloth, a waterproof film or the like. The foreside exterior topsheet 70F and the backside exterior topsheet 70R according to the embodiment is formed of an SMS nonwoven cloth of which a total weight is 15 g/m$^2$ and which is made of polypropylene.

The foreside exterior backsheet 80F and the backside exterior backsheet 80R are positioned on the outside at the time of wearing. Namely, these backsheets are disposed at a side which is spaced from a wearer's skin. An outer end of the longitudinal direction of the foreside exterior backsheet 80F and an outer end of the longitudinal direction of the backside exterior backsheet 80R are returned at a skin contact surface side, and are disposed so as to envelope the outer end of the longitudinal direction of the foreside exterior topsheet 70F (or the backside exterior topsheet 70R).

The frontside exterior backsheet 80F and the backside exterior backsheet 80R can be formed of an air-through nonwoven cloth, a span bond nonwoven cloth, an SMS nonwoven cloth, or a waterproof film or the like. The exterior backsheet according to the embodiment is formed of a span bond nonwoven cloth of 18 g/m$^2$ in total weight made of polypropylene.

The exterior body 1B is joined with the absorbent main body 1A in a part of a region which overlaps with the absorbent main body 1A. Of the region in the region in which the exterior body 1B and the absorbent main body 1A overlap with each other, in another region, the exterior body 1B and the absorbent main body 1A are not joined with each other, and in the region, a space 91 is formed between the exterior body 1B and the absorbent main body 1A. On a face in the outward direction's side of the disposable diaper 1, an opening unit 90 which communicates with the space 91 between the exterior body 1B and the absorbent main body 1A is formed. A structure of the opening unit 90 and the space 91 will be described later in detail.

The absorbent main body 1A includes a topsheet 10, an auxiliary sheet 15, an absorber backsheet, and a leakage preventing unit, and is disposed closer to the wearer's skin contact side than the exterior body 1B.

The topsheet 10 is a sheet that forms the skin contact surface that can be in direct contact with the skin of the wearer. The topsheet 10 is provided closer to the skin contact surface than the absorber 40. The topsheet 10 is formed by a liquid-permeable sheet, such as a hydrophilic nonwoven cloth and a hydrophilic woven cloth, an aperture plastic film, or an aperture hydrophobic nonwoven cloth. The topsheet 10 according to the embodiment is formed of a hydrophilic spun bond nonwoven cloth having a basis weight of 23 g/m² of polypropylene.

An auxiliary sheet 15 is joined with the non-skin contact surface side of the topsheet 10. The auxiliary sheet 15 is disposed between the topsheet 10 and the absorber 40. Providing the auxiliary sheet 15 makes it possible to increase the speed at which the bodily fluid is absorbed, and makes it possible to prevent reversal of the bodily fluid after absorption.

The topsheet 10 and the auxiliary sheet 15 according to the embodiment are joined by adhesive. The auxiliary sheet 15 is made of, for example, an air-through nonwoven cloth, an aperture film, or the like. The auxiliary sheet 15 according to the embodiment is formed of air-through nonwoven cloth (hydrophilic) having a basis weight of 30 g/m².

The absorber 40 has: a first absorption layer 41 which is positioned at a non-skin contact surface side of a wearer; and a second absorption layer 42 which is overlapped with the first absorption layer 41 and which is positioned at a skin contact surface side of the wearer. Between: a composite sheet on which the topsheet 10 and the auxiliary sheet 15 are joined with each other; and the absorber backsheet 30, the first absorption layer 41 and the second absorption layer 42 are joined with the absorber backsheet by a hot melt-type adhesive agent. The hot melt-type adhesive agent is applied to a respective one of the composite sheet and the backsheet, and for example, a total weight of 5 g/m² and 8 g/m² is applied by a spiral coating method.

The first absorption layer 41 and the second absorption layer 42 are respectively composed of cotton-like pulp and polymeric absorptive polymer (SAP). The first absorption layer 41 and the second absorption layer 42 can be formed, for example, by mixing the pulse of 100 g/m² to 500 g/m² and the SAP of 20 g/m² to 500 g/m² with each other. The first absorption layer 41 and the second absorption layer 42 according to the embodiment are formed by mixing the pulse of 280 g/m² and the SAP of 170 g/m².

In the first absorption layer 41, a central slit 45 and a pair of side slits 46 are formed. The central slit is formed at a center in a widthwise direction of the first absorption layer. The central slit 45 has a longitudinally elongated shape extending along the longitudinal direction L. The central slit 45 is formed in this manner, whereby a central portion in a widthwise direction of the absorber can be curved in a convex manner in the inward direction IN that is the wearer's side. Also, diffusion property of bodily fluid or the like in the longitudinal direction of the absorber is enhanced, the bodily fluid or the like is diffused in a wide range, and the absorption performance can be improved.

One pair of side slits 46 are respectively formed outside of the widthwise direction than the central slit 45. The side slits 46 each have a longitudinally elongated shape extending along the longitudinal direction L. The side slits 46 each are formed in the absorber 40 along the longitudinal direction L so as to curve in a convex manner in an outward direction OUT, namely, so that the absorber 40 curves in a convex manner which is opposite to the central slit 45.

When the disposable diaper 1 is worn, the crotch region S3 of the absorber is brought into contact with the wearer's crotch. By the wearer's legs or the like, a force is applied to the absorber from the outside of the widthwise direction toward the inside of the widthwise direction. When the force is applied to the absorber 40 from the outside of the widthwise direction to the inside of the widthwise direction, the absorber 40 deforms in the inward direction and in the outward direction on the basis of the central slit 45 and the side slits 46. A sectional shape along the widthwise direction W of the disposable diaper 1 deforms in a wavy shape, and the crotch region S3 of the absorber 40 is in a regularly folded state.

The absorber is folded in this manner, whereby the absorber 40 of the crotch region S3 is appropriately folded, making it possible to bring the absorber 40 and the excretion opening into contact with each other. Therefore, the absorption performance is enhanced, and a leakage of bodily fluid can be restrained.

The absorber backsheet 30 is provided at a non-skin contact surface side of the absorber 40. The absorber backsheet 30 is formed of a sheet such as a liquid-impermeable film (for example, polyethylene). The absorber backsheet 30 is disposed in an outward direction OUT than the absorber, and is formed of a liquid non-permeable. The absorber backsheet 30 is disposed so as to be extensive to the outside of the longitudinal direction than the absorber 40.

The absorber backsheet 30 is exposed on the non-skin contact side face between the foreside exterior body 1BF and the backside exterior body 1BR. In the region, the absorber backsheet 30 constitutes the face of the non-skin contact side of the disposable diaper 1.

The leakage preventing unit has a leakage preventing side sheet 32 and a leakage preventing elastic member 33, and is disposed along the longitudinal direction at a widthwise end of the absorber 40. The leakage preventing side sheet 32 is provided so as to integrally envelope the topsheet 10 and the absorber backsheet 30 at both side ends in the widthwise direction W of the absorber 40. The leakage preventing side sheet 32 is formed of a sheet such as a liquid impermeable nonwoven cloth. One end of the widthwise direction of the leakage preventing side sheet 32 is joined with a face of the non-skin surface side of the absorber backsheet 30, and the other end of the widthwise direction of the leakage preventing side sheet 32 is folded back from a lateral of absorber 40 in widthwise direction to the top sheet side, and is joined with a face of the skin contact surface side of the topsheet 10.

The leakage preventing side sheet 32 is joined with the topsheet or the like by a hot melt adhesive. In the embodiment, a plurality of hot melt adhesives was applied in total weight of 0.1 g/m² by bead coating method. In addition, as the leakage preventing side sheet 32, a sheet of a hydrophobic nonwoven cloth can be employed, and in the embodiment, an SMS nonwoven cloth having a basis weight of 15 g/m² of polypropylene was employed.

The leakage preventing elastic member 33 is adhered between the absorber backsheet 30 and the leakage preventing side sheet 32 in an expanded state. A hot melt adhesive can be exemplified as a means for bonding the leakage preventing elastic member. In the embodiment, Spandex is employed as the leakage preventing elastic member 33, and is directly applied by V slot method. More specifically, three leakage preventing elastic members 33 are each expanded and fixed with a thickness of 780 dtex and an expansion magnification of 2.3 times.

In the front waistline region S1 and the back waistline region S2, a waist gather 3 is provided. The waist gather 3 has an elongated waist elastic member 3A such as a synthetic rubber which is arranged so as to stretch along the widthwise direction W of the absorber 40. The waist gather 3 is continuous from one fore front waistline edge 4 which is positioned outside of the widthwise direction W of the disposable diaper 1 in the front waistline region S1 up to the other front waistline edge 4', and is also continuous from one back waistline edge 6 which is positioned outside of the widthwise direction of the disposable diaper 1 in the back waistline region S2 up to the other back waistline edge 6'.

The waist elastic member 3A is fixed to the foreside exterior topsheet 70F or the back exterior topsheet 70R and the exterior backsheet in a stretched state by way of an adhesive agent (for example, a hot melt-type adhesive agent). In the embodiment, the hot melt-type adhesive agent is applied by a V-slot approach.

The waist elastic member 3A is composed of spandex. Six waist elastic members 3A are respectively stretched and fixed at a thickness of 940 dtex and at an expansion magnification of 3.5 times in the vicinities of the waistline opening unit 8, and eight waist elastic members are respectively stretched and fixed to the front and back at a thickness of 780 dtex and at an expansion magnification of 3.0 times so as to be inner in the longitudinal direction than the elastic member. It is to be noted that the thickness, the expansion magnification, and the number of waist elastic members 3A can be variously set without being limited thereto.

At the periphery of the leg-hole opening unit 9, a leg gather 5 is provided. At least a part of the leg gather 5 is disposed along the leg-hole opening unit 9. The leg gather 5 is formed of: a front leg-hole elastic member 5F which is disposed in the front waistline region S1; and a back leg-hole elastic member 5R which is disposed across the back waistline region S2 and the crotch region S3.

The back leg-hole elastic member 5R is disposed from the back waistline region S2 to the crotch region S3, and is disposed so as to face the inside of the widthwise direction as it goes from the back waistline region S2 to the crotch region S3. The front leg-hole elastic member 5F is disposed along the widthwise direction in the front waistline region S1. The front leg-hole elastic member 5F and the back leg-hole elastic member 5R in an outer region in the widthwise direction than the absorber 40 and the front leg-hole elastic member 5 and the back leg-hole elastic member 5R that overlap with the absorber 40 move together, and functions to pull up the absorber 40 to the wearer's side.

The front leg-hole elastic member 5F is disposed between the foreside exterior topsheet 70F and the foreside exterior backsheet 80F, and the back leg-hole elastic member 5R is disposed between the backside exterior topsheet 70R and the backside exterior backsheet 80R. Also, the waist elastic member 3A is joined between the foreside exterior topsheet 70F or the backside exterior topsheet 70R and the foreside exterior backsheet 80F or the backside exterior backsheet 80R.

The front leg-hole elastic member 5F and the back leg-hole elastic member 5R are composed of spandex. Three front leg-hole elastic members 5F and three back leg-hole elastic members 5R are respectively fixed at a thickness of 780 dtex and at an expansion magnification of 3.0 times. It is to be noted that the thicknesses, the expansion magnifications, and the numbers of front leg-hole elastic members 5F and back leg-hole elastic members 5R can be variously set without being limited to the above.

The exterior body 1B is provided with: a shrink region R4 which is shrunk by the waist elastic member or the leg-hole elastic member; and a non-shrink region R5 which is not shrunk by the waist elastic member or the leg-hole elastic member. The shrink region is a region in which a shrink force of the elastic member is developed, whereby the exterior body 1B shrinks. The non-shrink region is a region in which the shrink force of the elastic member is not developed, and the exterior body 1B does not shrink, and includes a region in which, although the elastic member is disposed, its shrink force is not developed, as well as a region in which the elastic member is not disposed. In FIG. 3, the shrink region R4 and the non-shrink region R5 of the exterior body 1B are illustrated.

The leakage preventing elastic member 33 is disposed so as to substantially communicate with the leg gather in a planar view. The leakage preventing elastic member and the leg gather are disposed in this manner, whereby tightening can be carried out so as to surround the wearer's leg feeding, the fitting property of leg feeding is improved, and there can be attained an advantageous effect of preventing a displacement of the disposable diaper or a leakage therefrom.

In so far as a method of manufacturing the thus configured disposable diaper is concerned, the disposable diaper can be manufactured by the method including the steps of: molding the first absorption layer of the absorber; molding the second absorption layer of the absorber; integrating the first absorption layer and the second absorption layer with each other; conveying the absorber or the like by a belt conveyer or the like; and joining a sheet member such as a topsheet in the course of conveying. It is to be noted that other steps enable manufacturing in accordance with a publicly known manufacturing method.

It is to be noted that the respective members that constitute the disposable diaper 1 as mentioned above may employ any material described in Japanese Unexamined Patent Application Publication No. 2006-346439.

(2) Structure of Opening Unit

Next, a structure of the opening unit 90 will be described in detail. The opening unit 90 is formed on a face at the outward direction's side of the disposable diaper 1. The face at the outward direction's side of the absorbent main body 1A and the face at the inward direction's side of the exterior body 1B are partially jointed with each other via adhesive means such as a hot melt-type adhesive agent in the region in which the absorbent main body 1A and the exterior body 1B overlap with each other in a planer view.

FIG. 2 shows: a joint region R1 in which the absorbent main body 1A and the exterior body 1B are joined with each other; and a non-joint region R2 in which the absorbent article 1A and the exterior body 1B are not joined with each other. The joint region R1 is provided in a respective one of an outside end of the longitudinal direction and an end of the widthwise direction of the region in which the absorbent main body 1A and the exterior body 1B overlap with each other in a planar view. The non-joint region R2 is a portion other than the joint region, and is provided in a respective one of an inside end of the longitudinal direction and a central portion which is surrounded by the outside end of the longitudinal direction and the end of the widthwise direction, of the region in which the absorbent main body 1A and the exterior body 1B overlap with each other in a planar view. The joint region R1 is provided at a respective one of three edges which are adjacent to each other in a rectangular region in which the absorbent main body 1A and the exterior body 1B overlap with each other, and is formed in a substantially U-shape in a planar view.

The joint region R1 and the non-joint region R2 are provided in this manner; and therefore, the inside end of the longitudinal direction of the exterior body 1B is spaced from the absorbent main body 1A at the center in the widthwise direction. A portion at which the inside end of the longitudinal direction of the exterior body 1B and the absorbent main body 1A are spaced from each other is obtained as the opening unit 90. Specifically, the above portion is a portion at which the backside end of the foreside exterior body 1BF and the absorbent main body 1A are spaced from each other, and is also a portion at which the foreside end of the backside exterior body 1BR and the absorbent main body 1A are spaced from each other. The opening unit 90 is an opening which is surrounded by the absorbent main body 1A and the exterior body 1B. The opening unit 90 is provided in a respective one of the foreside exterior body 1BF and the backside exterior body 1BR.

The joint region R1 of the embodiment is provided in a respective one of a region which is 30 mm inside of the longitudinal direction from the outside end of the longitudinal direction of the absorbent main body 1A and in a region which is 40 mm inside of the longitudinal direction from each end of the widthwise direction of the absorbent main body 1A.

Outside of the longitudinal direction than the opening unit 90, the non-joint region R2 that constitutes the space 91 that communicates with the opening unit 90 is provided. When fingers or the like are inserted into the opening unit, the finger or the like can be housed in the non-joint region R2. The joint region R1 and the non-joint region R2 are provided in this way, whereby a pocket targeted to be pulled up can be formed.

A space for the pocket to be formed in the non-joint region R2 requires a size to an extent such that fingers of hands can be housed and the force can be easily applied. Specifically, it is sufficient if a length in the widthwise direction of the non-joint region R2 is 40 mm or more and if a length in the longitudinal direction of the non-joint region R2 is 40 mm. A length in the widthwise direction of the opening unit 90 is 40 mm, whereby the size is so large that three fingers and an area leading up to a first joint can be sufficiently included and thus the fingers are securely included in the pocket portion, and can pull up the diaper. More preferably, the length in the widthwise direction of the non-joint region R2 is 70 mm or more, and the length in the longitudinal direction of the non-joint region R2 is 50 mm.

Dimensions of the pocket at the front waistline region side of the embodiment are as follows. A length in the widthwise direction of the absorbent main body 1A is 20 mm, and a length in the longitudinal direction in which the absorbent main body 1A and the foreside exterior body 1BF overlap with each other is 100 mm. A distance between the outside ends in the widthwise direction of the joint region R1 that is positioned at each side in the widthwise direction is 190 mm, and a length in the widthwise direction of each joint region R1 is 40 mm. A length in the longitudinal direction of the joint region R1 is 90 mm. A length in the longitudinal direction of the joint region R1 extending in the widthwise direction at the foreside end is 30 mm. Therefore, in so far as internal dimensions of the pocket at an abdominal side is concerned, a length in the widthwise direction 110 mm, and a length in the longitudinal direction is 70 mm.

Also, dimensions of the pocket at the back waistline region side of the embodiment are as follows. A length in the widthwise direction of the absorbent main body 1A is 200 mm, and a length in the longitudinal direction in which the absorbent main body 1A and the backside exterior body 1B overlaps with each other is 150 mm. A distance between outside ends in the widthwise direction of the joint region R1 that is positioned at each side in the widthwise direction is 190 mm, and a length in the widthwise direction of each joint region R1 is 40 mm. A length in the longitudinal direction of the joint region R1 is 135 mm. A length in the longitudinal direction of the joint region R1 extending in the widthwise direction at the foreside end is 100 mm. Therefore, in so far as internal dimensions of the pocket at the abdominal side, a length in the widthwise direction is 110 mm, and a length in the longitudinal direction is 50 mm.

Incidentally, it is sufficient if the joint region R1 is provided at an outer circumference of the space in order to form a space for pocket, and the joint region may be continuously provided, or alternatively, may be provided to be partially intermittently discontinuous. Also, it is sufficient if a joint strength of the joint region R1 is a strength at which no slip-off occurs when the diaper is pulled up.

As a method of bonding the absorbent main body 1A and the exterior body 1B with each other, for example, these bodies can be joined by applying an adhesive agent such as a hot melt-type adhesive agent to the absorbent main body side. As an application method, these bodies can be joined by an adhesive agent which is applied in quantity of 10 g/m² in a control seam approach, can be joined by an adhesive agent which is applied in a spiral approach or a slot coater approach, or can be joined by heat sealing or sonic sealing, and the bonding method is not limited in particular.

Exterior faces to surround the inside space of the pocket are the exterior topsheet of the exterior body 1B and the absorber backsheet 30 of the absorbent main body 1A. The opening unit 90 is formed by the non-joint region in which the exterior body 1B and the absorbent main body 1A are not joined with each other, whereby simplification of the manufacturing process and reduction of the number of parts can be achieved in comparison with a structure to provide additional pocket.

Also, the absorber backsheet 30 is made of a liquid-permeable film. The film is low in frictional coefficient of surface and easily slips in finger in comparison with a nonwoven cloth. The inside space of the pocket is surrounded by such a film, whereby fingers easily slips along the surface of the film. Therefore, fingers are easily inserted into the opening unit, and the fingers that are inserted into the opening unit, thus making it easy to pull up the disposable diaper.

Also, in so far as the non-skin contact surface of the disposable diaper 1 is concerned, exposed sheet members are different depending on the outside in the longitudinal direction and the inside in the longitudinal direction than the opening unit 90. Specifically, the outside backsheet that constitutes the exterior body 1B is exposed to the outside of the longitudinal direction than the opening unit 90, and the absorber backsheet 30 that constitutes the absorbent main body 1A is exposed to the inside of the longitudinal direction than the opening unit 90. Thus, the opening unit 90 is easily grasped from the outside of the disposable diaper 1. For example, even in a situation in which the disposable diaper is hardly seen such as a situation in which a user has to use the diaper in a dark place, the user can easily grasp the pocket position by touch. It is possible to verify the position of the pocket with a touch sense, there is no need for time to search for the pocket, and fingers can be easily inserted.

Also, the opening unit 90 is provided in the overlap region R3 that overlaps with the absorber 40. The overlap region is a region which overlaps with the absorber 40 in a thickness direction. The overlap region is based on a concept including an overlapping region in a state in which another member is interposed with respect to the absorber as well as an overlapping region while coming into contact with the absorber. In addition, in a mode in which the absorber 40 has a plurality of absorption layers (for example, the first absorption layer 41 and the second absorption layer 42), the overlap region R3 is a region which overlaps with at least either of the absorption layers. FIG. 3 illustrates the overlap region. Further, it is sufficient if at least a part of the opening unit is disposed in the overlap region, and the entire opening unit may not be disposed in the overlap region.

The overlap region that overlaps with the absorber is high in rigidity in comparison with a region in which no absorber is disposed, and the shrink force of the exterior body 1B is hardly developed by the rigidity of the absorber. The opening unit is provided in the overlap region, whereby a space provided between the exterior body 1B and the absorbent main body 1A is utilized while excessive shrink or twisting of the exterior body 1B due to shrink of the waistline elastic member or the like is restrained, and fingers are hooked in this pocket space, whereby the pants can be pulled up in an upward direction. In this manner, displacement in the transverse direction of the absorber or displacement or the like in the longitudinal direction is corrected, and in a finely stretched state, the absorbent main body 1A can be appropriately fitted to the body, thus making it possible to sufficiently have absorption performance.

Also, for example, if the opening unit is formed in the vicinity of the waistline opening unit, the opening unit is spaced from the excretion opening contact region of the absorber; and therefore, the force in an attempt to pull up the diaper via the pockets is hardly applied to the absorber that has become heavy in weight by absorbing bodily fluid, and there may be a case in which the entire disposable diaper cannot be easily pulled up. However, the opening unit is disposed in the overlap region that overlaps with the absorber; and therefore, even in a case where the absorber that has absorbed bodily fluid becomes heavy in weight, the force to pull up the diaper easily acts on the absorber, and the entire disposable diaper can be easily pulled up.

In addition, the opening unit is formed in the overlap region; and therefore, the position of the opening unit is located downward in its worn state in comparison with a structure in which the opening unit has been formed in the vicinity of the waistline opening unit. Therefore, the range of lifting up the arms can be reduced at the time of pulling up, and a burden on the wearer due to lifting up and down of the arms can be mitigated. In a state in which the wearer has worn the disposable diaper, the opening unit is positioned at the lowest side of the non-joint region; and therefore, the wearer easily hooks his or her fingers by the opening unit by lowering his or her arms from an upper side, and it is possible to easily pull up the disposable diaper or to adjust the position of the disposable diaper.

In addition, the opening unit is provided in the shrink region to be shrunk by the leg-hole elastic member as an elastic member. The opening unit is provided in the shrink region, whereby the opening unit easily shrinks and closes, making it possible to restrain a failure such as incorrect hooking of fingers or the like at the time of wearing.

Further, the opening unit 90 is formed by: the shrink region R4 to be shrunk by the leg-hole elastic member of the exterior body 1B; and the absorbent main body 1A. The shrink region R4 of the exterior body 1B shrinks, and the absorbent main body 1A does not shrink, only the exterior body side shrinks at the time of wearing; and therefore, the opening unit 90 easily opens, and fingers are easily inserted.

Furthermore, the space (the inside space of the pocket) 91 that communicates with the opening unit 90 is surrounded by the shrink region R4 of the exterior body 1B and the absorbent main body 1A. At the exterior body 1B to cover the inside space of this pocket, the shrink region R4 to be shrunk by the leg-hole elastic member and the shrink region R4 to be shrunk by the waist elastic member are provided. Therefore, the exterior body to cover the inside space of the pocket shrinks; and hence, a shrunk portion of the exterior body 1B is easily hooked and grasped by fingers, and operability is improved. In particular, a plurality of elastic members are provided while intervals of elastic members which constitute the shrink region are 15 mm, whereby fingers are easily hooked between the elastic members, and the user easily grasps the diaper. Further, the shrink region to surround the space that communicates with the opening unit (the inside space of the pocket) is formed by the leg-hole elastic member or the waistline elastic member, whereby the number of parts can be reduced in comparison with the structure to provide additional elastic member.

Furthermore, although, in the embodiment, the exterior body 1B is configured to be shrunk by the elastic member, for example, a sheet member which constitutes the exterior body 1B (the foreside exterior topsheet and/or the foreside exterior backsheet) may be structured by an elastic sheet so as to thereby shrink the exterior body 1B.

Further, the opening unit is formed in the overlap region, whereby the exterior body 1B and the absorbent main body 1A are spaced from each other in the overlap region. Thus, the exterior body 1B and the absorbent main body 1A are spaced from each other, whereby, even in a case where the exterior body 1B is shrunk by the waistline elastic member or the like, it is possible to restrain acting of the shrink force on the absorber. Therefore, it is possible to alleviate shrink of the absorber due to the elastic member that is provided at the exterior body 1B. Accordingly, the width of the absorber can be kept to be large, the visual sense of safety in absorption can be felt, an occurrence of wrinkles of the absorber can be restrained, and the absorption performance can be improved.

It is to be noted that, although in the embodiment, at the exterior body 1B, the shrink region is adjacent to the inside space of the pocket, the non-shrink region may be adjacent to the inside space of the pocket.

Moreover, in so far as the absorber of the embodiment is concerned, in its worn state, the absorber 40 deforms in the inward direction and in the outward direction on the basis of the central slit 45 and the side slits 46, and the sectional shape along the widthwise direction W deforms in a wavy shape. The central portion in the widthwise direction of the absorber 40 deforms in a convex shape, thereby making it possible to bring the absorber 40 into intimate contact with the wearer, enhance the absorption performance, and restrain a leakage of bodily fluid. Further. the opening unit to hook fingers is provided between the exterior body 1B and the absorbent main body 1A, and the diaper is pulled up by utilizing the pockets at the time of wearing, thereby making it possible to enhance intimacy of the crotch portion more significantly.

(3) Modification Examples

Next, Modification Examples will be described in detail with reference to FIG. 6 to FIG. 9. It is to be noted that, in the following description, only matters which are different from those of the embodiment will be explained, and like constituent elements of the embodiment are designated by like reference numerals, and a duplicate description thereof is omitted.

Figure 6:
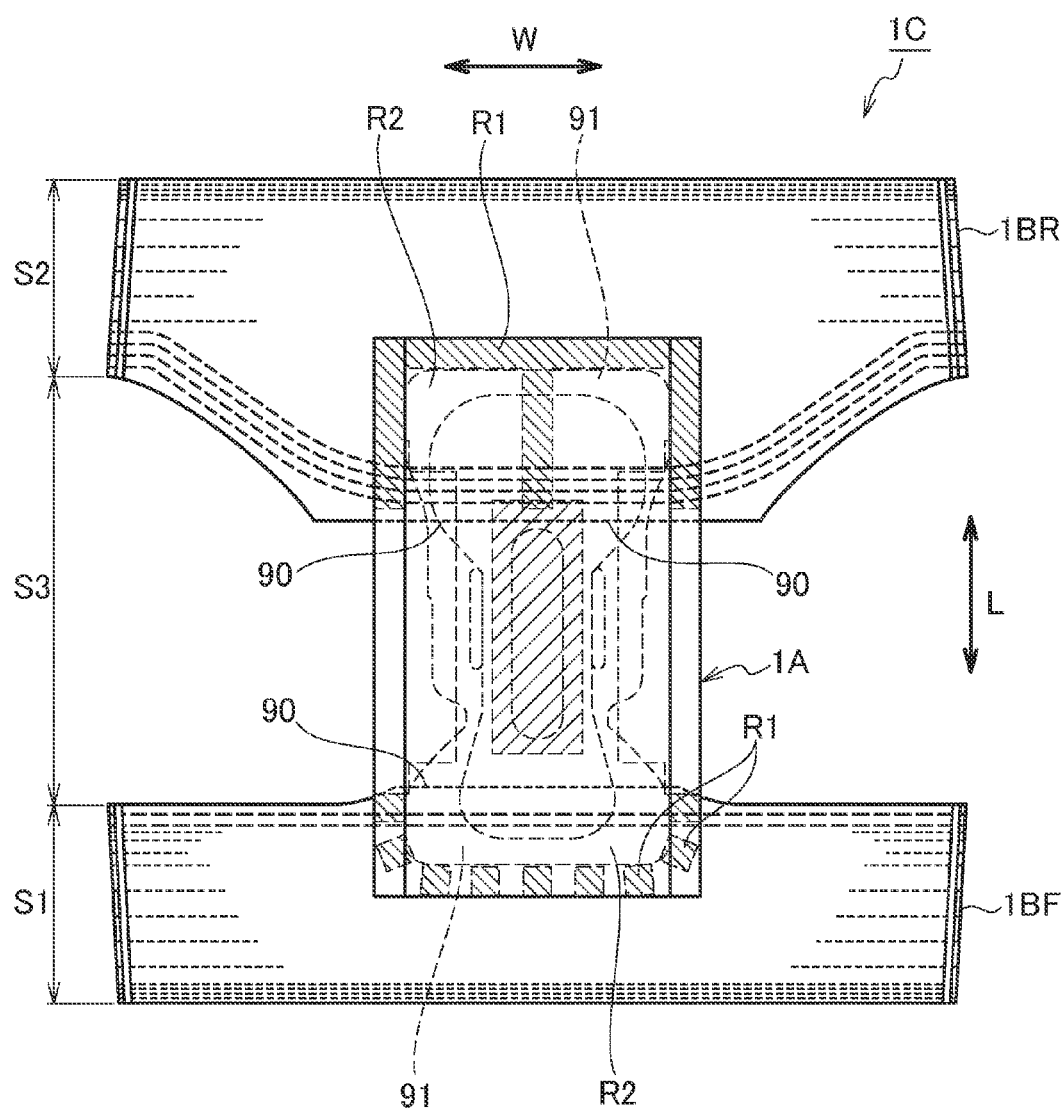
FIG. 6 is an exploded plan view of a disposable diaper according to Modification Example 1.

FIG. 6 is a plan view of a disposable diaper 1C according to Modification Examples 1. In so far as the disposable diaper according to Modification Example 1 is concerned, in a front waistline region S1, a joint region R1 to join a foreside exterior body 1BF and an absorbent main body 1A with each other is discontinuously provided, and in a back waistline region S2, two opening units 90, a respective one of which is formed between a backside exterior body 1BR and the absorbent main body 1A, are formed.

The joint region R1 to join the foreside exterior body 1BF and the absorbent article 1A with each other is discontinuously provided, and a force in an attempt to pull up the disposable diaper is transmitted via the joint region R1 that is discontinuously provided. For example, if the joint region R1 is provided in a dotted manner so as to draw an ellipse all over a widthwise direction, even in a case where one site such as a center or a side part or the like of the disposable diaper is grasped and pulled up, the force is transmitted to only the joint region R1, and the force is transmitted in a well-balanced manner as a whole. Therefore, an absorber is easily pulled up in well-balanced manner at the left and right.

For example, if the joint region R1 is continuously provided, the force in an attempt to pull up the disposable diaper is easily transmitted to only an adjacent portion which is grasped by fingers, and is pulled up in a manner in which the force is biased to that portion. However, the joint region R1 is discontinuously provided, whereby the entire diaper can be pulled up in a well-balanced manner. It is to be noted that the joint region R1 that is discontinuously shaped may be provided along a longitudinal direction or may be provided along a widthwise direction.

Also, a plurality of opening units 90 are provided in at least one of the front waistline region S1 and the back waistline region S2, whereby a plurality of fingers can be hooked and pulled up by a respective one of the opening units, or alternatively, both hands each can be hooked and pulled up by the respective one of the opening units. Also, in a case where a width of the absorbent main body 1A is large, if a width of the respective one of the opening units of a pocket is too long, a grasp is prone to be unstable. However, the opening unit 90 are divided into a plurality of sections, thereby making it possible to form the length in the widthwise direction of a respective one of pockets to be small, and making it easy to ensure stabilization when fingers are inserted into one pocket.

It is to be noted that the number of opening units 90 is not limited in particular. Also, a plurality of opening units are provided to be adjacent to each other in the widthwise direction, whereby fingers of one hand are easily inserted into the plurality of opening units, and the diaper can be easily pulled up even by one hand. In addition, in the disposable diaper in which three or more opening units are disposed adjacent to each other in the widthwise direction, the diaper is pulled up via a central opening unit, and is pulled up in a respective oblique upper direction via left and right opening units thereof, whereby the entire disposable diaper can be uniformly pulled up.

Figure 7:
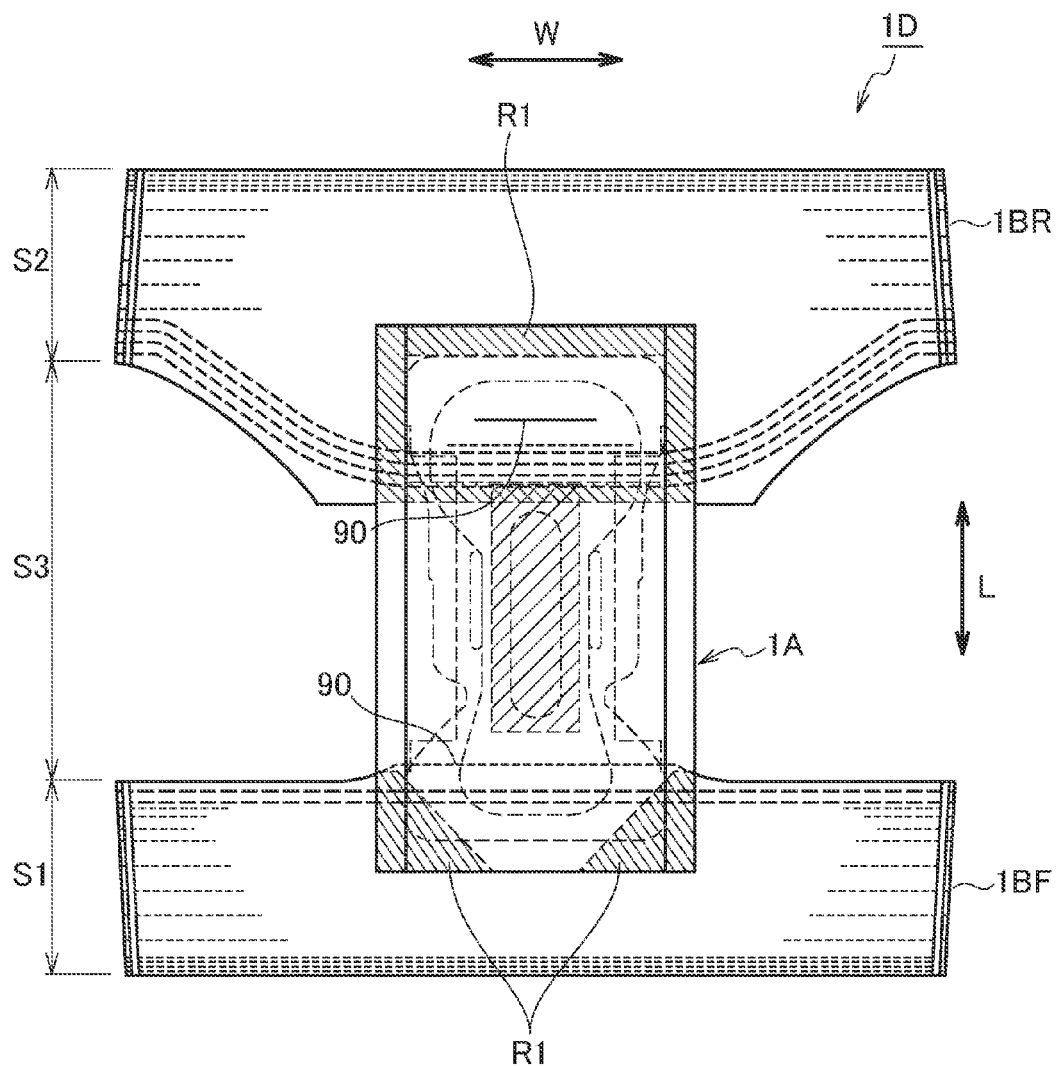
FIG. 7 is an exploded plan view of a disposable diaper according to Modification Example 2.

FIG. 7 is a plan view of a disposable diaper 1D according to Modification Example 2. In so far as the disposable diaper 1D according to Modification Example 2 is concerned, in the front waistline region S1, a center in the widthwise direction of a foreside end of the absorbent main body 1A is not joined with the foreside exterior body 1BF, and the joint region R1 is separated in a widthwise direction. The joint region R1 is separated in the widthwise direction in this manner; and therefore, even in a case where a depth of a pocket (a length in a longitudinal direction) is small, fingers can be inserted through the pocket, and the fingers can be deeply inserted. Therefore, even in a case the depth of the pocket (the length in the longitudinal direction) is small, a force is easily applied, and the diaper can be strongly pulled up.

A pair of joint regions R1 of the front waistline region S1 are disposed to be spaced from each other at the left and right, and a distance between the pair of joint regions R1 becomes gradually shorter toward a forward direction. That is, in so far as an inside space of a pocket which is formed by a non-joint region R2 is concerned, a length in a widthwise direction is formed to be small toward an upper side in a state in which the disposable diaper is worn. According to such a structure, the space of the pocket is obliquely inclined; and therefore, the diaper is easily pulled up to an oblique upper left or an oblique upper right as well as an upper direction.

Also, in so far as the disposable diaper 1D according to Modification Example 2 is concerned, in the back waistline region S2, the joint region R1 is provided all over an outer circumference of a region in which the backside exterior body 1B and the absorbent main body 1A overlap with each other. An opening unit 90 is a cutout which is formed in the exterior body 1B, and is formed so as to couple to the non-joint region R2 that is surrounded by the joint region R1.

Figure 8:
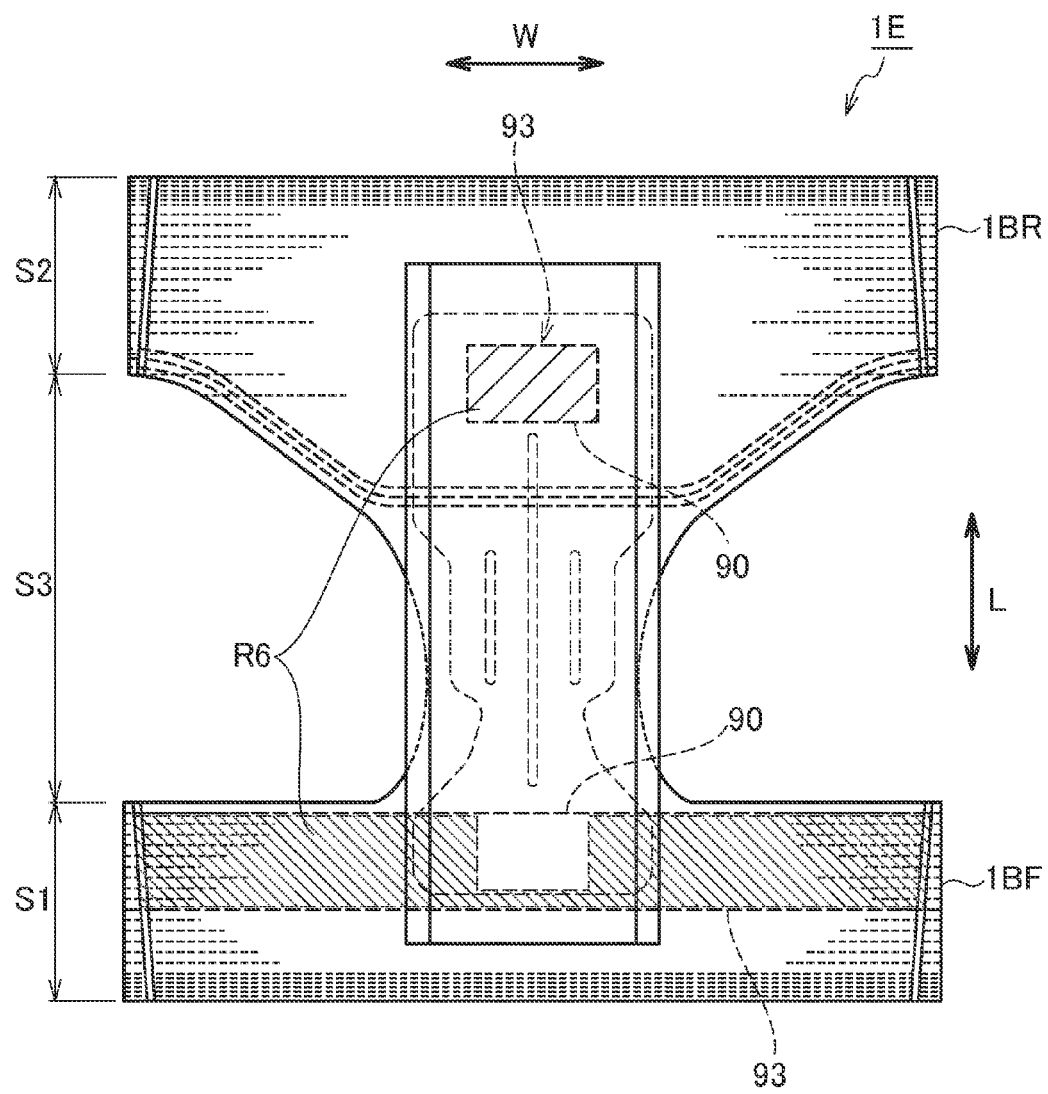
FIG. 8 is an exploded plan view of a disposable diaper according to Modification Example 3.

FIG. 8 is a plan view of a disposable diaper 1E according to Modification Example 3. In so far as the disposable diaper 1E according to Modification Example 3 is concerned, pockets and opening units are formed by a pocket sheet member 93 which is joined at an outward direction's side of an exterior backsheet. It is to be noted that the pocket sheet member 93 may be structured so as to form the opening units and the pockets by folding the pocket sheet member 93 or by overlapping the pocket sheet member 93, by way of only the pocket sheet member 93, or alternatively, the pocket sheet member may be structured to be joined with the exterior body 1B so as to form the pockets and opening units together with the exterior body.

The exterior body 1B has: exterior sheets (a foreside exterior topsheet 70F, a backside exterior topsheet 70R, a foreside exterior topsheet 80F, and a backside exterior backsheet 80R), a respective one of which is joined with the absorbent main body 1A and has at least a front waistline region and a back waistline region; and a pocket sheet member 93 which is disposed in an outward direction than the exterior sheets. FIG. 8 shows a joint region R6 between the exterior body 1B and the pocket sheet member 93.

The pocket sheet member 93 is joined with a face at the outward direction's side of the exterior body 1B, whereby a pocket having an opening unit 90 can be formed. A position of the pocket sheet member 93 is appropriately determined, whereby an opening unit can be provided at a desired position. Further, the pocket sheet member is joined with the existing absorbent article, whereby an opening unit can be formed.

The pocket sheet member 93 in the back waistline region is joined with the face at the outward direction's side of the exterior body 1B in a state in which the member is folded twice or more. The opening unit 90 and the inside space of the pocket are surrounded by the pocket sheet members.

On the other hand, the pocket sheet member 93 in the front waistline region is joined with the exterior body 1B in a single layered state (in an unfolded state). The opening unit 90 and the inside space of the pocket are respectively surrounded by the pocket sheet member and the exterior body.

Further, a length in the widthwise direction of the pocket sheet member 93 in the back waistline region S2 is smaller than that of the absorbent main body 1A. According to such pocket sheet member 93, the opening unit 90 is not only structured to be disposed along the widthwise direction, but also can be disposed to be oblique with respect to the widthwise direction.

For example, there may be employed a structure in which a pair of pocket sheet members 93 which are spaced from each other at the left and right are joined with the exterior body 1B so that the opening unit of the respective pocket sheet members face the inside in the widthwise direction. According to such a structure, in front waistline region S1, hands are carried to a lower abdominal part and then fingers are hooked in the opening units, whereby the diaper can be pulled up obliquely. Also, in the back waistline region S2, hands are carried to the buttocks and then fingers are hooked in the opening units, and the diaper can be pulled up obliquely. Also, in the back waistline region S2, hands are carried to the buttocks and then fingers are hooked in the opening unit 90, and the diaper can be pulled up obliquely.

In addition, in so far as the disposable diaper 1E according to Modification Example 3 is concerned, in the front waistline region S1, the pocket sheet member 93 is provided all over the widthwise direction of the exterior body 1B. By such a pocket sheet member as well, a pocket can be formed between the exterior body and the pocket sheet member or between the pocket sheet members.

In addition, there may be employed a structure in which an elastic member is provided at the pocket sheet member so that the pocket sheet member 93 shrinks.

Figure 9:
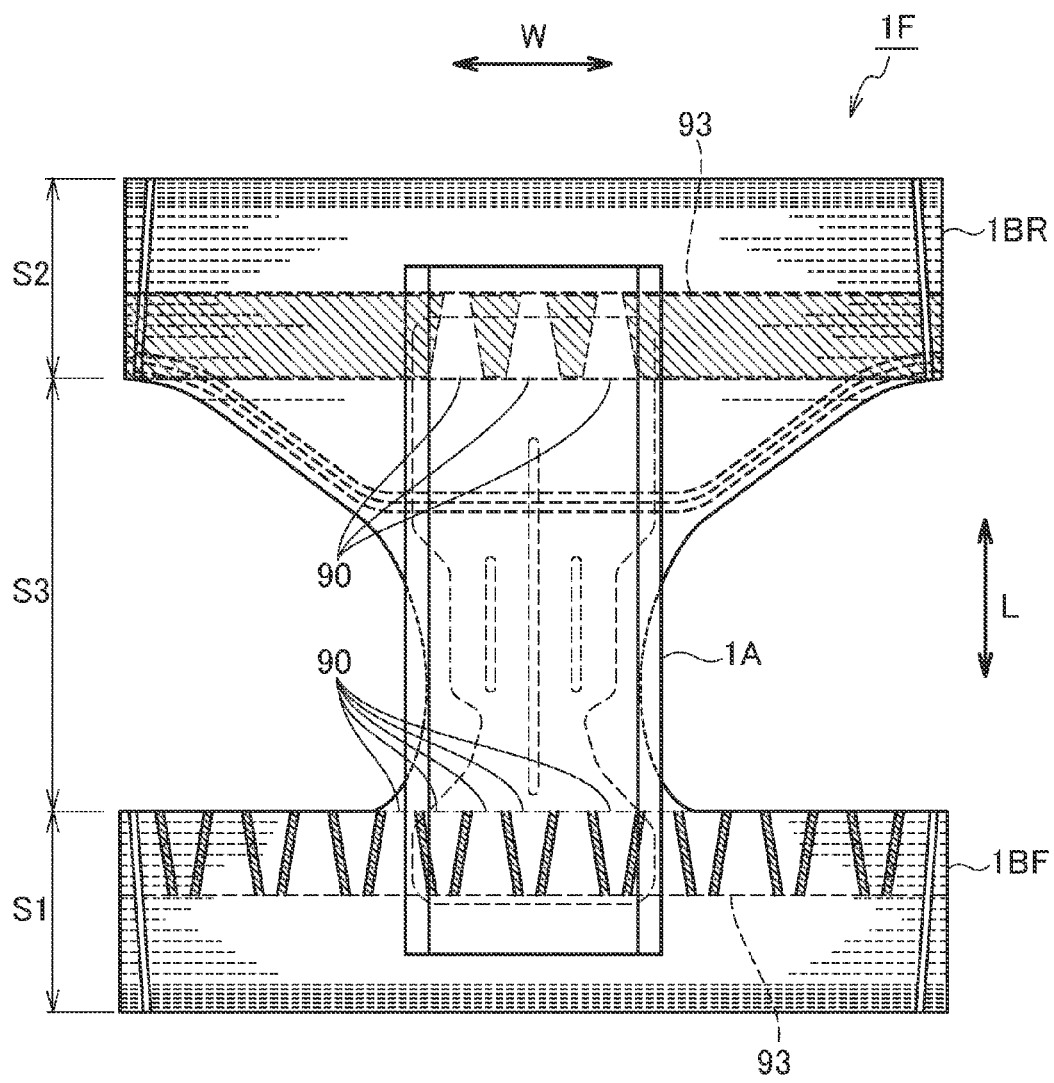
FIG. 9 is an exploded plan view of a disposable diaper according to Modification Example 4.

FIG. 9 is a plan view of a disposable diaper 1F according to Modification Example 4. In so far as the disposable diaper 1F according to Modification Example 4 is concerned, opening units 90 and pockets are formed by the pocket sheet 93 that is joined with the outer direction's side of the exterior backsheet.

In so far as the pocket sheet member 93 of the disposable diaper 1F according to Modification Example 4 is concerned, the pocket sheet member 93 is provided all over the widthwise direction of the exterior body 1B. Also, the pocket sheet member 93 of Modification Example 4 is composed of a belt-shaped stretchable sheet.

The pocket sheet member 93 has elasticity, and is partly joined with the exterior body. A part of the pocket sheet member 93 is partially joined with the face at the outward direction's side of the exterior body 1B, whereby fingers can be inserted into a non-joint portion at which the pocket sheet member 93 and the exterior body 1B are not joined with each other, and it is possible to pull up the diaper or correct displacement of the absorber while stretching the elastic sheet.

(4) Other Embodiments

As described above, although the contents of the present invention were disclosed through the embodiments of the present invention, it is not to be understood that the statements and drawings forming a part of this disclosure limit the present invention. From this disclosure, a variety of alternate modes, examples, and operational techniques would be self-evident to one skilled in the art.

For example, while, in the foregoing embodiment, the disposable diaper of the pants-type was described by way of example, the present invention is not limited thereto, and may be applied to an open-type disposable diaper, an incontinence pad, and a sanitary napkin or the like.

Also, the opening unit may be provided in the non-shrink region

Further, the absorber 40 has a bi-layered structure of the first absorbent layer 41 and the second absorbent layer 42, but the absorber 40 of the worn article according to further embodiments may be configured from a single layer or may be configured from three or more layers As described above, needless to say, the present invention includes various embodiments and the like not described here. Accordingly, the scope of the present invention is defined only by the appended claims in view of the above description.

The entire contents of Japanese Patent Application No. 2012-219391 (filed on Oct. 1, 2012) are incorporated in the present specification by reference.

INDUSTRIAL APPLICABILITY

An absorbent article which is capable of being easily pulled up by a wearer or the like can be provided.

REFERENCE SIGNS LIST

1 . . . Disposable diaper
1A . . . Absorbent main body
1B . . . Exterior body
1BF . . . Foreside exterior body
1BR . . . Backside exterior body
3 . . . Waist gather
3A . . . Waist elastic member
4, 4' . . . Front waistline edge
5 . . . Leg gather
5F . . . Front leg-hole elastic member
5R . . . Back leg-hole elastic member
6, 6' . . . Back waistline edge
8 . . . Waistline opening unit
9 . . . Leg-hole opening unit
10 . . . Topsheet
15 . . . Auxiliary sheet
30 . . . Absorber backsheet
32 . . . Leakage preventing side sheets
33 . . . Leakage preventing elastic member
40 . . . Absorber
41 . . . First absorption layer
42 . . . Second absorption layer
45 . . . Central slit
46 . . . Side slits
70F . . . Foreside exterior topsheet
70R . . . Backside exterior topsheet
80F . . . Foreside exterior backsheet
80R . . . Backside exterior backsheet
90 . . . Opening unit
91 . . . Space
93 . . . Pocket sheet member
S1 . . . Front waistline region
S2 . . . Back waistline region
S3 . . . Crotch region
R1 . . . Joint region
R2 . . . Non-joint region
R3 . . . Overlap region
R4 . . . Shrink region
R5 . . . Non-shrink region

The invention claimed is:
1. An absorbent article having:
a longitudinal direction configured to extent to a body foreside and a body backside of a wearer;
a widthwise direction which is orthogonal to the longitudinal direction;
an inward direction configured to face a wearer; and
an outward direction opposite to the inward direction,
the absorbent article comprising:
a front waistline region;
a back waistline region; and a crotch region which is positioned between the front waistline region and the back waistline region, the absorbent article comprising:

an absorbent main body having an absorber which is disposed at least in the crotch region; and an exterior body including an exterior body sheet which is disposed in the outward direction than the absorbent main body;

wherein a plurality of opening units into which a finger can be inserted are formed in a face at the outward direction's side of the absorbent article;

the plurality of opening units are provided in an overlap region which overlaps with the absorber; and the plurality of the opening units are provided in at least one of the front waistline region and the back waistline region.

2. The absorbent article according to claim 1, wherein an elastic member which stretches and shrinks in the widthwise direction is provided in a respective one of the front waistline region and the back waistline region of the exterior body;

the exterior body comprises:

a shrink region which is shrunk by the elastic member; and a non-shrink region which does not shrunk due to the elastic member; and the plurality of opening units are provided in the shrink region.

3. The absorbent article according to claim 2 wherein the exterior body comprises:

a foreside exterior body which is joined with the absorbent main body and which is disposed in the front waistline region;

a backside exterior body which is joined with the absorbent main body and which is disposed in the back waistline region; and the opening unit is a non-joint portion which is provided at a backside end of the overlap region of the foreside exterior body and at which the foreside exterior body and the absorbent main body are not joined with each other.

4. The absorbent article according to claim 2, wherein the exterior body comprises:

a foreside exterior body which is joined with the absorbent main body and which is disposed in the front waistline region; and a backside exterior body which is joined with the absorbent main body and which is disposed in the back waistline region; and the opening unit is a non-joint portion which is provided at a foreside end of the overlap region of the backside exterior body and at which the backside exterior body and the absorbent main body are not joined with each other.

5. The absorbent article according to claim 2, wherein the exterior body sheet comprises:

an exterior sheet having at least the front waistline region and the back waistline region; and a pocket sheet member which is disposed in the outward direction than the exterior sheet and which forms the plurality of opening units.

6. The absorbent article according to claim 1, wherein the exterior body comprises:

a foreside exterior body which is joined with the absorbent main body and which is disposed in the front waistline region;

a backside exterior body which is joined with the absorbent main body and which is disposed in the back waistline region; and the plurality of opening units are non-joint portions which are provided at a backside end of the overlap region of the foreside exterior body and at which the foreside exterior body and the absorbent main body are not joined with each other.

7. The absorbent article according to claim 6, wherein the absorbent main body comprises a liquid-impermeable film which is disposed on a face at the outer direction's side of the absorbent main body.

8. The absorbent article according to claim 1, any wherein the exterior body comprises:

a foreside exterior body which is joined with the absorbent main body and which is disposed in the front waistline region; and a backside exterior body which is joined with the absorbent main body and which is disposed in the back waistline region; and the plurality of opening units are non-joint portions which are provided at a foreside end of the overlap region of the backside exterior body and at which the backside exterior body and the absorbent main body are not joined with each other.

9. The absorbent article according to claim 8, wherein the absorbent main body comprises a liquid-impermeable film which is disposed on a face at the outer direction's side of the absorbent main body.

10. The absorbent article according to claim 1, wherein the exterior body sheet comprises:

an exterior sheet having at least the front waistline region and the back waistline region; and a pocket sheet member which is disposed in the outward direction than the exterior sheet and which forms the plurality of opening units.

* * * * *